United States Patent
Gunji (10) Patent No.: US 9,086,316 B2
(45) Date of Patent: Jul. 21, 2015

(54) SPECTROMETRY DEVICE

(75) Inventor: Masahide Gunji, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 14/384,034

(22) PCT Filed: Mar. 27, 2012

(86) PCT No.: PCT/JP2012/057852
§ 371 (c)(1),
(2), (4) Date: Nov. 6, 2014

(87) PCT Pub. No.: WO2013/145112
PCT Pub. Date: Oct. 3, 2013

(65) Prior Publication Data
US 2015/0109610 A1    Apr. 23, 2015

(51) Int. Cl.
*G01N 21/00* (2006.01)
*G01J 3/02* (2006.01)
*G01N 30/74* (2006.01)

(52) U.S. Cl.
CPC .............. *G01J 3/0286* (2013.01); *G01N 30/74* (2013.01)

(58) Field of Classification Search
CPC ... H01J 37/32935; G01N 21/64; G01N 21/68; G01N 30/74; G01N 2015/1037
USPC ...................... 356/300–445, 72–73
See application file for complete search history.

(56) References Cited

U.S. PATENT DOCUMENTS 6,072,459 A * 6/2000 Asakawa et al. .............. 345/101

FOREIGN PATENT DOCUMENTS

| JP | 63-198832 A | 8/1988 |
|---|---|---|
| JP | 2000-205953 A | 7/2000 |
| JP | 2006-047210 A | 2/2006 |
| JP | 2007-064632 A | 3/2007 |
| JP | 4448808 B2 | 4/2010 |
| JP | 2011-002310 A | 1/2011 |

OTHER PUBLICATIONS

International Search Report dated Apr. 24, 2012, issued in corresponding Application No. PCT/JP2012/057852. (3 pages).

* cited by examiner

*Primary Examiner* — Abdullahi Nur
(74) *Attorney, Agent, or Firm* — Westerman, Hattori, Daniels & Adrian, LLP (57) ABSTRACT

A control unit for controlling the temperature of a spectrometer to be constant stores a first temperature coefficient indicating a proportion of a temperature change of the spectrometer to a room temperature change and a second temperature coefficient indicating a proportion of the temperature change of the spectrometer to a change in the air volume of blower means, and calculates the amount of change in the air volume of the blower means necessary to offset a change in the temperature of the spectrometer from a predetermined constant temperature, by using the first temperature coefficient and the second temperature coefficient, and controls driving of the blower means based on the calculated amount of change in the air volume.

8 Claims, 5 Drawing Sheets

SPECTROMETRY DEVICE

TECHNICAL FIELD

The present invention relates to a spectrometry device including a light source unit, a spectroscopic element for dispersing light entering from the light source unit, and a photodetector for detecting the dispersed light. The spectrometry device includes an absorbance measurement device and a fluorescence measurement device. These spectrometry devices may each be used as an independent measurement device, or may be used as a detector of an analysis device such as a liquid chromatograph and a flow injection analyzer.

BACKGROUND ART

As an example of using the spectrometry device as a detector of a liquid chromatograph, a photodiode array absorbance detector that uses a photodiode array (PDA) as a photodetector of a spectrometer may be cited. The photodiode array absorbance detector measures the absorption spectrum of an analysis sample flowing into a flow cell by radiating light emitted by a light source on the flow cell through which effluent of the liquid chromatograph flows, and dispersing the light which has passed through the flow cell by a diffraction grating and converging the light on the photodiode array.

Normally, a lamp is used as the light source, and a light source chamber housing the lamp and, in addition, cooling means for cooling the light source chamber are provided. This is because, normally, an optimum surface temperature for realizing optimum light emission is set to the lamp used as the light source, and the light source chamber has to be cooled in such a way that the lamp surface is at this temperature. As the cooling means, a forced air cooling fan, which is inexpensive and has a high cooling efficiency, is used in many cases.

In the case of a spectrophotometer that adopts a single-beam measurement technique such as the photodiode array absorbance detector, if the ambient room temperature around the device changes, the amount of light entering the photodiode array changes due to a change in the amount of light of the light source or deformation of the spectrometer by thermal expansion, for example, and baseline noise or drift may thereby occur. Accordingly, to increase the sensitivity of the spectrophotometer, it is important to stabilize the light entering the photodiode array.

There is an example where, to suppress a change in the amount of light of the light source caused by a change in the room temperature, the number of rotations of the cooling fan is changed according to a change in the room temperature and the temperature of the light source is kept constant to thereby suppress a change in the amount of light of the light source and reduce the noise/drift (for example, see Patent Document 1).

PRIOR ART DOCUMENTS

Patent Documents

Patent Document 1: Japanese Patent No. 4448808

DISCLOSURE OF THE INVENTION

Problems to be Solved by the Invention

However, according to this method, although a change in the amount of light of the light source caused by a change in the room temperature may be suppressed, the temperature change at the spectrometer cannot be controlled. Thus, an optical element of the spectrometer, a diffraction grating or the like is deformed by thermal expansion due to a change in the temperature of the spectrometer, and the spectrum of light dispersed and converged on the photodiode array is changed. As a result, noise or drift occurs in chromatography.

A problem caused by a change in the temperature of the spectrometer has been described by citing a photodiode array absorbance detector as an example, but this problem is not confined to the photodiode array absorbance detector, and is a common problem shared by spectrometry devices provided with a spectrometer.

The present invention aims to reduce the influence of a change in the room temperature, such as baseline noise/drift, in the output of the spectrometer of a spectrometry device.

Means for Solving the Problems

The present invention reduces baseline noise/drift or the like that is caused by a change in the room temperature, by executing the following means.

(1) A light source chamber and a spectrometer are thermally conducted, and the heat of the light source chamber is caused to be transferred to the spectrometer.

(2) The room temperature is monitored by using temperature measurement means, and when the room temperature is changed, the amount of cooling air to the light source chamber is changed accordingly, and the temperature of the spectrometer is kept constant through a change in the temperature of the light source chamber.

The means of (1) and (2) described above are necessary for the present invention. In that case, since according to the present invention, the temperature of the light source chamber is not controlled to be constant, the amount of light of the light source is changed. In the case of using a photodiode array as a photodetector, even if the amount of light of the light source is changed, a change in the amount of light caused by the light source may be corrected by selecting light of a specific wavelength from the spectrum of light entering the photodiode array and monitoring the amount of light by taking the wavelength as reference light. Accordingly, in the case where a change in the amount of light of the light source influences a measurement result, the following means (3) is added.

(3) A photodiode array is used as a photodetector, light of a specific wavelength is selected from the spectrum of light entering the photodiode array, the amount of light is monitored by taking the wavelength as reference light, and a change in the amount of light of the light source is corrected. Any wavelength may be selected as the wavelength used for monitoring the amount of light so long as the optical path inside the spectrometer does not pass through a sample. However, in the case where the optical path inside the spectrometer does pass through a sample, a wavelength which is not absorbed by the sample is selected as the specific wavelength.

The present invention adopts a view that, in order to suppress noise/drift induced by a change in the room temperature, it is more important to keep the temperature of the spectrometer constant and to suppress a change in the spectrum which is the spectrometer output than to keep the temperature of the light source constant and to suppress a change in the amount of light.

A spectrometry device of the present invention includes a light source unit accommodating a light source inside a light source chamber, a spectrometer including, inside a housing including an optical window through which light from the light source unit is to enter, a spectroscopic element for dispersing light entering from the light source unit and a photodetector for detecting dispersed light, the spectrometer being in contact with the light source unit in a thermally conducted state, a cover for covering the light source unit and the spectrometer, blower means provided to an opening of the cover, for blowing cooling air from outside the cover into the light source unit, a first temperature sensor for detecting a temperature of the cooling air from the blower means, a second temperature sensor for detecting a temperature of the spectrometer, and a control unit for adjusting an air volume of the blower means based on a detected temperature of the first temperature sensor in such a way that a detected temperature of the second temperature sensor will be at a predetermined constant temperature Furthermore, the control unit includes a first temperature coefficient storage unit for storing a first temperature coefficient indicating a proportion of a change in the detected temperature of the second temperature sensor to a change in the detected temperature of the first temperature sensor, a second temperature coefficient storage unit for storing a second temperature coefficient indicating a proportion of the change in the detected temperature of the second temperature sensor to a change in the air volume of the blower means, an air volume change amount calculation unit for calculating an amount of change in the air volume of the blower means that is necessary to offset a change in the detected temperature of the second temperature sensor from the predetermined constant temperature, by using the first temperature coefficient stored in the first temperature coefficient storage unit and the second temperature coefficient stored in the second temperature coefficient storage unit, and a blower means drive control unit for controlling driving of the blower means based on the amount of change in the air volume calculated by the air volume change amount calculation unit.

In other words, the control unit stores a first temperature coefficient indicating a proportion of a temperature change of the spectrometer to a room temperature change and a second temperature coefficient indicating a proportion of the temperature change of the spectrometer to a change in the air volume of blower means, and calculates the amount of change in the air volume of the blower means necessary to offset a change in the temperature of the spectrometer from a predetermined constant temperature, by using the first temperature coefficient and the second temperature coefficient, and controls driving of the blower means based on the calculated amount of change in the air volume.

According to a preferred mode, the control unit further includes a feedback control unit for controlling driving of the blower means after drive control of the blower means based on the amount of change in the air volume calculated by the air volume change amount calculation unit, in such a way that the detected temperature of the second temperature sensor will be at the predetermined constant temperature, and the blower means drive control unit further controls driving of the blower means based on an instruction from the feedback control unit. This assumes a case where a temperature difference between the temperature of the spectrometer and the predetermined constant temperature is present when drive control of the blower means based on the amount of change in the air volume calculated by the air volume change amount calculation unit is simply performed. In this case, the temperature of the spectrometer is detected by the second temperature sensor, and feedback control that is performed through driving the blower means to eliminate the temperature difference is added. The accuracy of temperature control for the spectrometer is thereby increased.

According to the present invention, the temperature of the light source unit is not controlled to be constant. Rather, the temperature of the spectrometer is kept constant by changing the temperature of the light source unit. Accordingly, the amount of light is changed due to the change in the temperature of the light source unit. In a mode of correcting the change in the amount of light, the photodetector is a photodiode array, a data processing unit for processing a detection output of the photodetector is provided, and the data processing unit includes a light amount change correction unit for correcting a change in an amount of light from the light source unit based on an output of a specific light receiving element of the photodiode array. The specific light receiving element is a light receiving element for detecting a specific wavelength among dispersed wavelengths. In the case where light to enter the photodetector is light which passes through a sample solution, the specific wavelength is preferably a wavelength that is not absorbed by the sample solution.

According to an embodiment, as an example of a case where the spectrometer is caused to be in contact with the light source unit in a thermally conducted state, the light source chamber of the light source unit and the housing of the spectrometer that are both made of thermally conductive material and are in contact with each other through a spacer made of thermally conductive material arranged therebetween may be cited.

The first temperature sensor is for detecting the room temperature, and the room temperature here is the temperature of the cooling air from the blower means. The preferred arrangement position of the first temperature sensor for detecting the temperature of the cooling air is a position, inside the cover, that is to be directly hit by the cooling air.

The second temperature sensor is for detecting the temperature of the spectrometer, and, as an example, it may be attached being in contact with an inner wall of the housing of the spectrometer. The temperature of the spectrometer may be more accurately detected in the case where the housing is made of thermally conductive material.

The spectrometry device of the present invention may be used for various purposes but is typically used as a detector of a liquid chromatograph. In this case, the spectrometry device is configured to include a sample cell on an optical path inside the spectrometer, the sample cell allowing a measurement target sample solution from a liquid chromatograph to flow through.

When used as a detector of a liquid chromatograph, fluorescence measurement is performed in addition to absorbance measurement. In the mode of performing absorbance measurement, the photodetector is arranged at a position where light passing through the sample cell is to be detected, and the spectrometry device is an absorbance measurement device.

Effects of the Invention

According to the present invention, the temperature of the spectrometer is kept constant, and in the case where spectrum measurement is performed by the spectrometer, a change in the spectrum due to deformation of an optical element inside the spectrometer by thermal expansion is suppressed.

Since temperature adjustment is performed with the temperature of the spectrometer as a reference, although the surface temperature of the light source changes by a change in the room temperature and the amount of light of the light source changes, the change in the amount of light of the light source may be corrected as necessary, and, in reducing baseline noise/drift, this is more effective than controlling the surface temperature of the light source to be constant.

MODE FOR CARRYING OUT THE INVENTION

Figure 1:
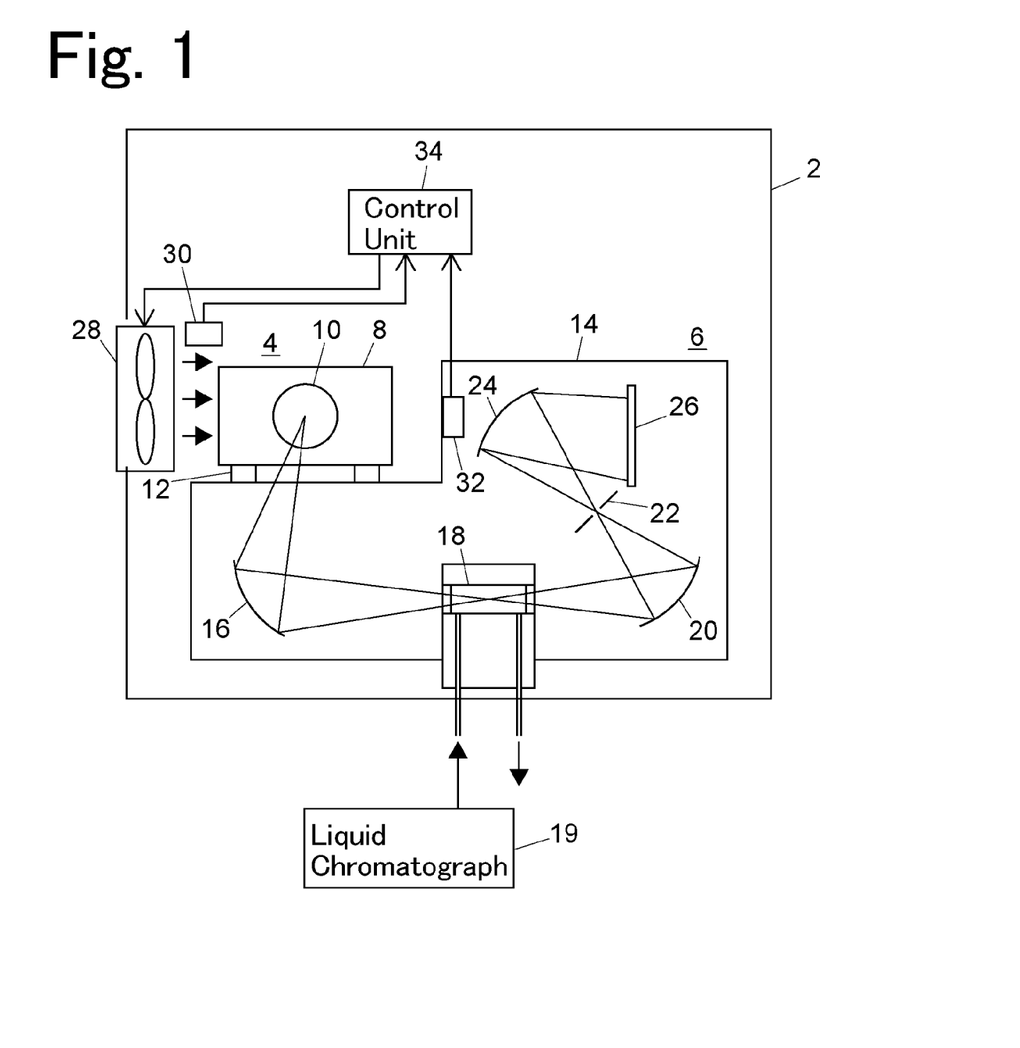
FIG. 1 is a configuration diagram schematically showing an embodiment.

FIG. 1 is a diagram schematically showing a configuration according an embodiment. Here, a photodiode array absorbance detector for a liquid chromatograph including a multi-wavelength detection function is described as an example of a spectrometry device, but the present invention is not restricted to such, and may also be used as other spectrometry devices such as a fluorescence measurement device.

This spectrometry device includes inside a space covered by a cover 2, as main constituent components, a light source unit 4 and a spectrometer 6. To prevent external light from entering as stray light, the surface of the cover 2 is made of aluminum on which a black anodic oxide coating is formed, that is, on which so-called alumite processing is applied.

A light source 10 is provided inside a light source chamber 8 of the light source unit 4. The housing forming the light source chamber 8 is made of thermally conductive metal, and is formed of aluminum, for example. Although not particularly restrictive, a discharge lamp such as a deuterium lamp and a tungsten lamp is used as the light source 10. Light emitted from the light source 10 is radiated on the spectrometer 6 through a window plate (not shown) and a spacer 12. The spacer 12 is also made of thermally conductive metal, and is formed of for example stainless steel.

The spectrometer 6 includes, inside its housing 14, in the order of passing of light from the light source unit 4, a window plate of an optical window (not shown), a converging mirror 16, a flow cell 18, a converging mirror 20, a slit 22, a concave diffraction grating 24 as a spectroscopic element, and a photodiode array 26 as a photodetector. The housing 14 is also made of thermally conductive metal, and is formed of for example aluminum. Light from the light source chamber 8 is converged by the converging mirror 16 at the flow cell 18. The light which has passed through the flow cell 18 is converged at the slit 22 by the converging mirror 20. The light which has passed through the slit 22 is dispersed by the diffraction grating 24. The photodiode array 26 detects the light intensity of wavelengths by light receiving elements at respective positions with respect to light of a plurality of wavelengths dispersed by the diffraction grating 24.

Effluent from a liquid chromatograph 19 is supplied to the flow cell 18 as a sample. The spectrometry device of the present embodiment is a photodiode array absorbance detector as the detector of the liquid chromatograph 19.

Those mentioned above as the material of the housing of the light source chamber 8, the spacer 12, and the housing 14 of the spectrometer are only examples, and the material is not particularly limited as long as the material is thermally conductive metal. Aluminum, stainless steel, brass, copper, iron and the like may be selected and used as appropriate.

The light source chamber 8 and the spectrometer 6 are arranged with the spacer 12 made of thermally conductive metal arranged therebetween to achieve good thermal conduction, and are in contact with each other in a thermally conducted state. The spacer 12 may be of an integrated type having an aperture for passing light. Since the thermal resistance is smaller as the cross section of the portion where heat flows from the light source chamber 8 to the spectrometer 6 is larger, an integrated spacer with a large cross section is convenient. However, the spacer 12 may also be formed from a plurality of separate blocks. Also, the light source chamber 8 and the spectrometer 6 may be arranged in direct contact with each other without the spacer 12 arranged therebetween.

To cool the light source chamber 8, a fan 28 as blower means for blowing cooling air from outside the cover 2 into the light source chamber 8 is provided at an opening of the cover 2.

A thermistor 30 is provided inside the cover 2 as a first temperature sensor for detecting, as the room temperature, the temperature of the cooling air from the fan 28. The thermistor 30 is preferably arranged at a position which is directly hit by the cooling air.

A thermistor 32 is provided as a second temperature sensor for detecting the temperature of the spectrometer 6. The thermistor 32 is attached being in contact with the inner wall of the housing 14 of the spectrometer 6. Since, in the spectrometer 6, the concave diffraction grating 24, which is a spectroscopic element, is most affected by the temperature, the thermistor 32 is preferably arranged near the concave diffraction grating 24.

A control unit 34 is provided to control the detected temperature of the thermistor 32 for measuring the temperature of the spectrometer to be at a predetermined constant temperature. The thermistor 30 and the thermistor 32 are connected to the control unit 34, and the control unit 34 controls the air volume of the fan 28 according to the output signals (temperatures) of the thermistors 30 and 32. The control unit 34 is mainly configured by a microcomputer including a CPU, a RAM, a ROM, an EPROM (or an EEPROM), or the like. In the present embodiment, the control unit 34 is arranged inside the cover 2 and is utilized as a control unit dedicated to the spectrometry device, but the control unit 34 may also be arranged outside the cover 2. In the case where the control unit 34 is to be arranged outside the cover 2, the control unit 34 may be realized by other than the CPU and the like dedicated to the spectrometry device, such as a control device of a liquid chromatograph to which the spectrometry device is connected, an external work station and a personal computer.

Figure 2:
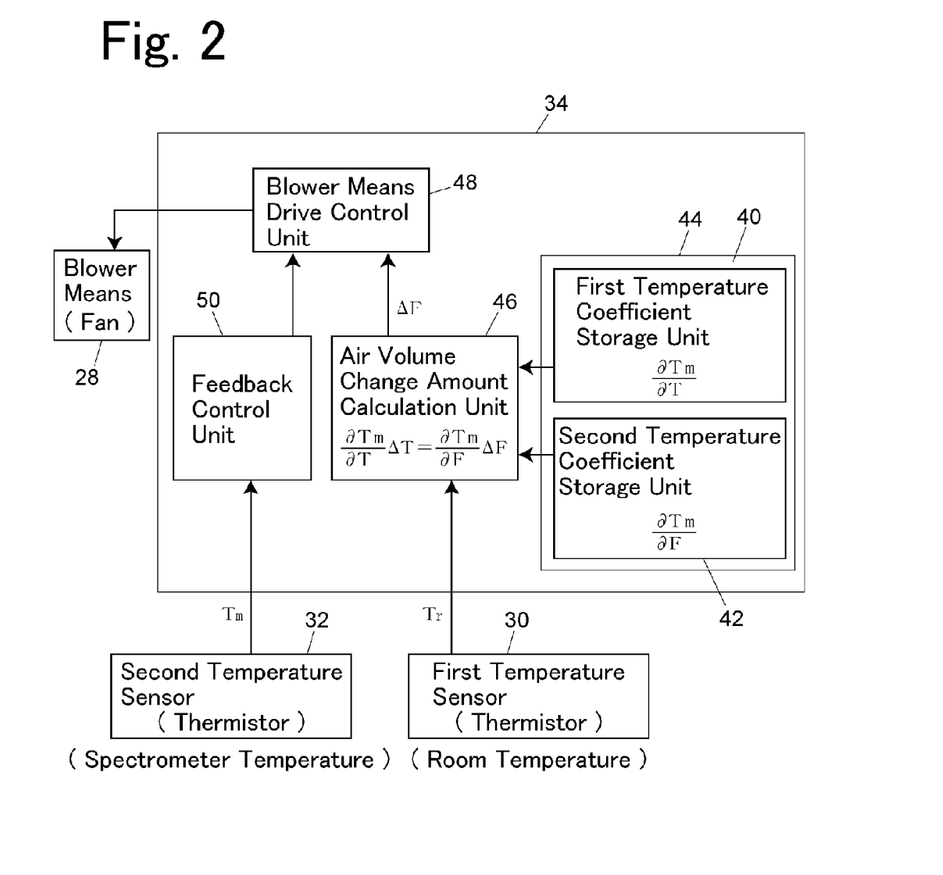
FIG. 2 is a block diagram showing a control system of the embodiment.

The control unit 34 is configured as shown in FIG. 2. This configuration includes a function to be executed by a program installed in a microcomputer and data stored in an EPROM. The outline of control by the control unit 34 is as follows.

The light source chamber 8 is connected to the spectrometer 6 by the metal spacer 12 with good thermal conductivity, and thus, the heat from the light source chamber 8 is transferred to the spectrometer 6. In the case where the air volume of the cooling fan 28 and the room temperature are constant, the temperature of the spectrometer 6 is at a certain constant temperature Tm. This Tm is determined by an air volume F of the fan 28 and a room temperature Tr that is detected by the thermistor 30, and thus, Tm(F, Tr) is true.

Now, when it is assumed that the room temperature Tr changed by ΔT, Tm is $$T_m(F, T_r + \Delta T) \cong T_m(F, T_r) + \frac{\partial T_m}{\partial T_r} \cdot \Delta T$$

and to keep Tm constant, the control unit 34 changes the air volume F of the fan 28 in such a way as to offset $(\partial T_m/\partial T_r) \cdot \Delta T$. That is, when the amount of change in the air volume of the fan 28 is given as $\Delta F$, an air volume change amount calculation unit 46 of the control unit 34 extracts an amount of change $\Delta T$ in the room temperature Tr from a detection output of the thermistor 30, extracts a derivative $(\partial T_m/\partial T_r)$ as a first temperature coefficient from a first temperature coefficient storage unit 40 and a derivative $(\partial T_m/\partial F)$ as a second temperature coefficient from a second temperature coefficient storage unit 42, and calculates, based on a relational expression $$\frac{\partial T_m}{\partial T_r} \cdot \Delta T = \frac{\partial T_m}{\partial F} \cdot \Delta F \quad (1)$$

an amount of change $\Delta F$ in the air volume of the fan 28. A blower means drive control unit 48 changes the air volume of the fan 28 based on the amount of change $\Delta F$ in the air volume calculated by the air volume change amount calculation unit 46.

Figure 3:
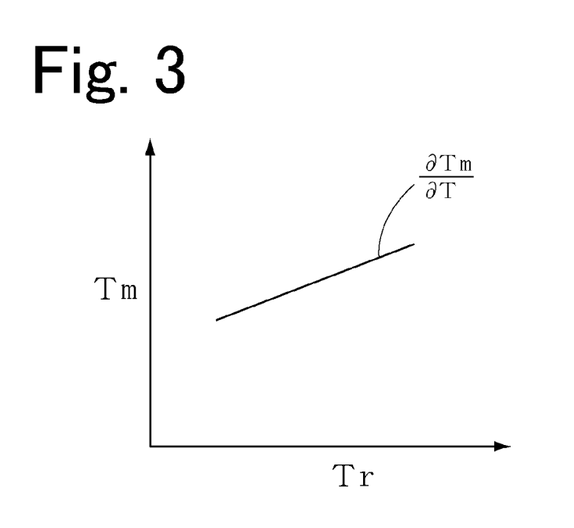
FIG. 3 is a graph showing a relationship between a spectrometer temperature Tm and a room temperature Tr.
Figure 4:
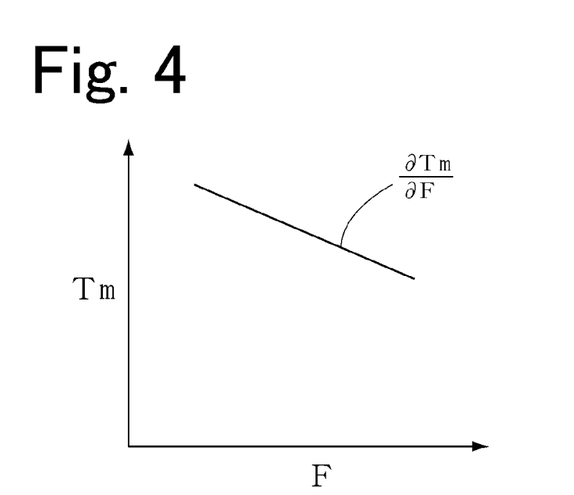
FIG. 4 is a graph showing a relationship between the spectrometer temperature Tm and an air volume F of a fan.

The derivative $(\partial T_m/\partial T_r)$, which is the first temperature coefficient, at this time is obtained by actually measuring preliminarily the relationship between the room temperature Tr that is detected by the thermistor 30 and the spectrometer temperature Tm that is detected by the thermistor 32 as shown in FIG. 3 under several conditions with respect to an assembled spectrometry device, and is stored in the first temperature coefficient storage unit 40. In the same manner, the other derivative $(\partial T_m/\partial F)$, which is the second temperature coefficient, is obtained by actually measuring preliminarily the relationship between the air volume F of the fan 28 and the spectrometer temperature Tm that is detected by the thermistor 32 as shown in FIG. 4 under several conditions with respect to an assembled spectrometry device, and is stored in the second temperature coefficient storage unit 42. In FIGS. 3 and 4, the relation of the spectrometer temperature Tm to the room temperature Tr and the relation of the spectrometer temperature Tm to the air volume F of the fan 28 are shown to change linearly, but this is only schematic. The basic spectrometer temperature Tm in a normal use state is set to 20° C., for example, and the first temperature coefficient $(\partial T_m/\partial T_r)$ and the second temperature coefficient $(\partial T_m/\partial F)$ are obtained as the derivatives of the temperature.

The first temperature coefficient storage unit 40 and the second temperature coefficient storage unit 42 are realized by an EPROM as an example of a memory. An electrically erasable EEPROM or another memory device may also be used instead of the EPROM.

Figure 5:
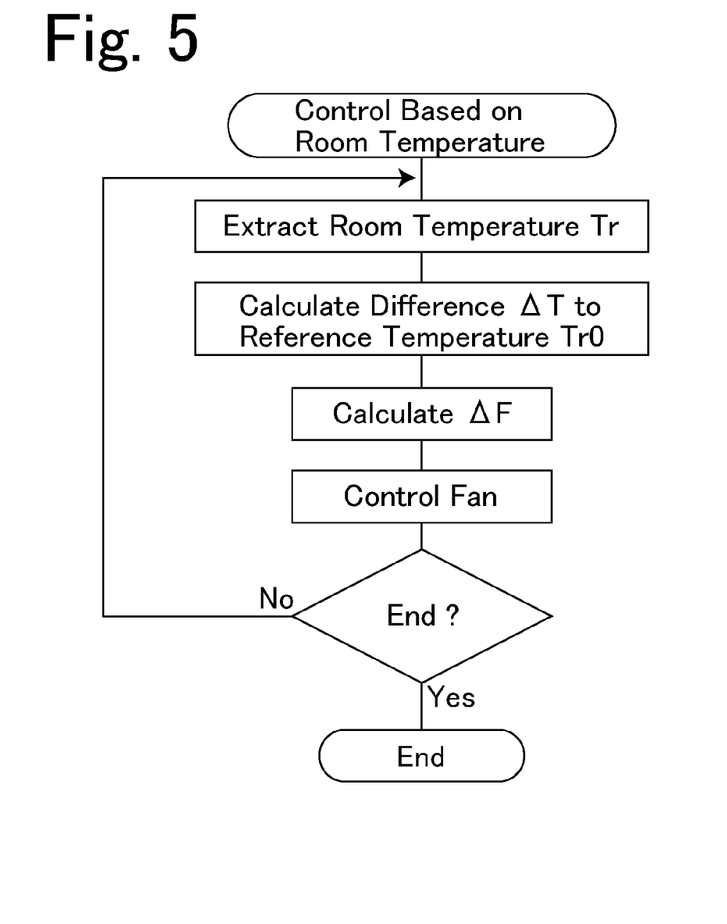
FIG. 5 is a flow chart showing a control operation based on a room temperature Tr according to an embodiment.

An operation of controlling the air volume of the fan 28 according to a change in the room temperature Tr by formula (1) above in such a way that the temperature Tm of the spectrometer 14 becomes constant is shown in FIG. 5. The control unit 34 extracts the room temperature Tr from the thermistor 30, compares the same with a reference temperature Tr0 set in advance, such as 20° C., and calculates a difference $\Delta T$. The amount of change $\Delta F$ in the air volume of the fan 28 for offsetting the $\Delta T$ is calculated by formula (1) above, and the fan 28 is driven according to the amount of change $\Delta F$ in the air volume. This operation is continuously performed during a measurement operation.

Basically, the air volume of the fan 28 is controlled according to a change in the room temperature Tr by formula (1) above in such a way that the temperature Tm of the spectrometer 14 becomes constant. However, since the first temperature coefficient $(\partial T_m/\partial T_r)$ and the second temperature coefficient $(\partial T_m/\partial F)$ are actually approximate values obtained under several measurement conditions, it is difficult to keep the temperature Tm of the spectrometer 6 absolutely constant only by formula (1) above.

Accordingly, a feedback control unit 50 is provided to correct the difference between a temperature change (an approximate value) of the spectrometer 6 that is achieved by changing the air volume of the fan 28 based on the amount of change $\Delta F$ in the air volume obtained by formula (1) above and the actual temperature change of the spectrometer. The feedback control unit 50 monitors the temperature Tm of the spectrometer 6 by the thermistor 32. Then, in the case where there is a difference between the temperature Tm of the spectrometer 6 and a predetermined constant temperature after a specific time, for example, after several minutes, has elapsed since the blower means drive control unit 48 performed the operation of changing the air volume of the fan 28 based on the amount of change $\Delta F$ in the air volume calculated by the air volume change amount calculation unit 46, the air volume F of the fan 28 is corrected to minimize the difference. The correction of the air volume F of the fan 28 by the feedback control unit 50 is also performed through the blower means drive control unit 48.

Figure 6:
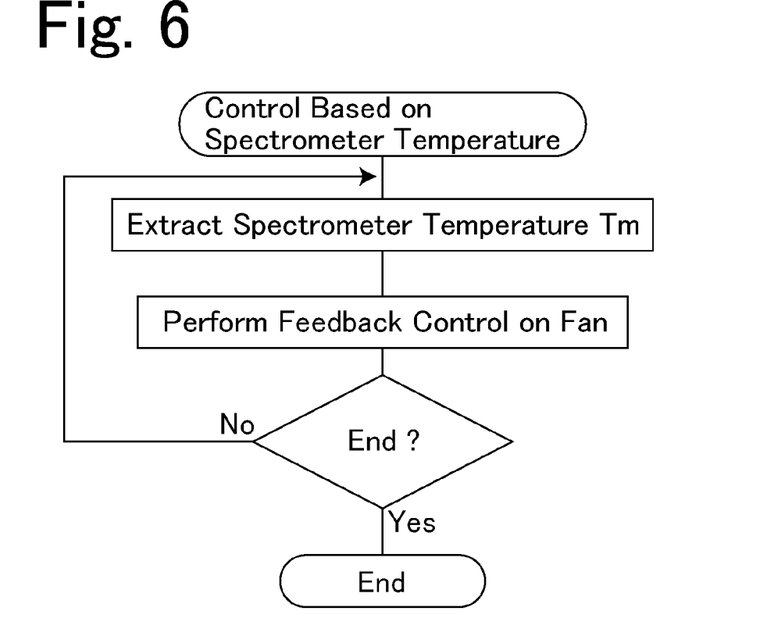
FIG. 6 is a flow chart showing a feedback operation based on a spectrometer temperature Tm according to the embodiment.

The operation of feedback control by the feedback control unit 50 is shown in FIG. 6. After a specific time has elapsed since control of the air volume of the fan 28 according to a change in the room temperature Tr was performed according to formula (1), the control unit 34 extracts the spectrometer temperature Tm from the thermistor 32, and in the case where the temperature is not at a predetermined constant temperature to be achieved, feedback control is performed by changing the air volume of the fan 28 in such a way that the spectrometer temperature Tm will be at the constant temperature. This feedback control is also continuously performed during the measurement operation.

With this method, the temperature of the spectrometer 6 may be kept constant, and a change in the spectrum on the photodiode array 26 caused by a change in the room temperature Tr may be suppressed.

According to the present invention, since the temperature of the light source chamber 8 is not controlled to be constant, the temperature of the light source chamber 8 changes to cause the spectrometer temperature to be constant. To prevent a change in the amount of light caused by a change in the temperature of the light source chamber 8 from affecting a measurement result, light amount correction means is provided in a preferred embodiment.

The outline is shown in FIG. 6. A data processing unit 60 is provided to process the detection output of the photodiode array 26, which is a photodetector, and to perform spectrum analysis or calculation of a quantitative value. The data processing unit 60 includes a light amount change correction unit 62 for correcting a change in the amount of light from the light source unit 4 based on an output of a specific light receiving element of the photodiode array 26.

Figure 7:
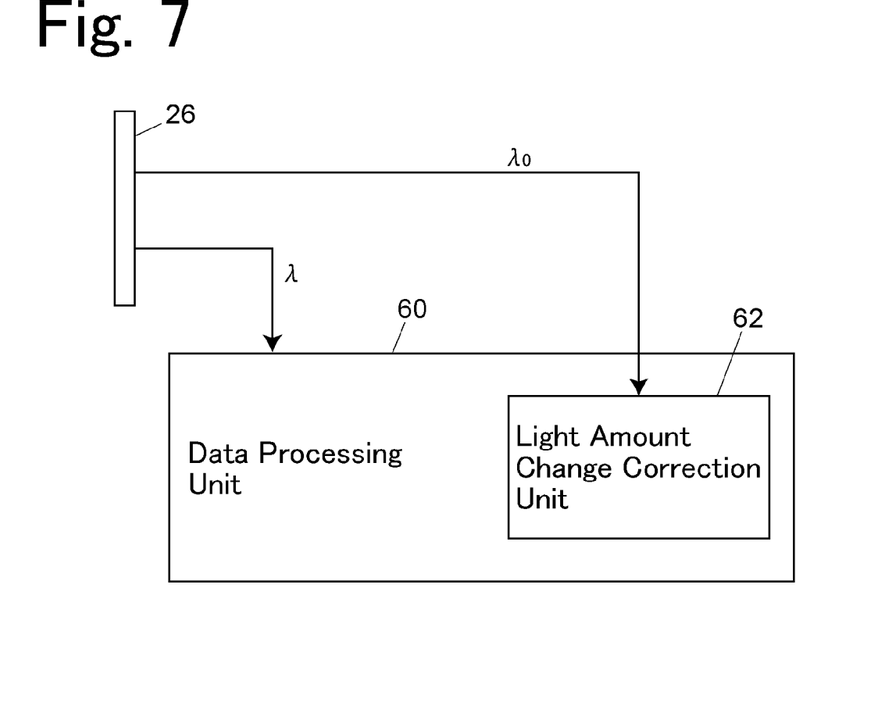
FIG. 7 is a flow chart showing a light amount change correction operation according to an embodiment.

Specifically, the light amount change correction unit 62 selects light of a wavelength that is not absorbed by a sample flowing through the flow cell 18 from the spectrum of light entering the photodiode array 26, and corrects a change in the amount of light of the light source 10 with the light of the wavelength thereof as reference light. By performing this light amount change correction, the baseline may be stabilized in a better manner than by controlling the temperature of the light source 10 to be constant.

In the case where this spectrometry device is used as a detector of a liquid chromatograph, as in this embodiment, the data processing unit 60 is realized by a computer provided to the liquid chromatograph.

Even in the case where such correction of a change in the amount of light caused by a change in the temperature of the light source is not performed, a change in the spectrum on the photodiode array 26 is suppressed by keeping the temperature of the spectrometer 6 constant, and thus, the baseline is more stabilized than in a case where no control is performed with respect to the air volume of the fan 28.

DESCRIPTION OF REFERENCE SIGNS

2: Cover
4: Light source unit
6: Spectrometer
8: Light source chamber
10: Light source
12: Spacer
14: Housing of spectrometer
19: Liquid chromatograph
24: Concave diffraction grating
26: Photodiode array
28: Fan
30, 32: Thermistor
34: Control unit
40: First temperature coefficient storage unit
42: Second temperature coefficient storage unit
46: Air volume change amount calculation unit
48: Blower means drive control unit
50: Feedback control unit
60: Data processing unit
62: Light amount change correction unit

What is claimed is:

1. A spectrometry device comprising:
a light source unit accommodating a light source inside a light source chamber;
a spectrometer including, inside a housing including an optical window through which light from the light source unit is to enter, a spectroscopic element for dispersing light entering from the light source unit and a photodetector for detecting dispersed light, the spectrometer being in contact with the light source unit in a thermally conducted state;
a cover for covering the light source unit and the spectrometer;
blower means provided to an opening of the cover, for blowing cooling air from outside the cover into the light source unit;
a first temperature sensor for detecting a temperature of the cooling air from the blower means;
a second temperature sensor for detecting a temperature of the spectrometer; and
a control unit for adjusting an air volume of the blower means based on a detected temperature of the first temperature sensor in such a way that a detected temperature of the second temperature sensor will be at a predetermined constant temperature,
wherein the control unit includes
a first temperature coefficient storage unit for storing a first temperature coefficient indicating a proportion of a change in the detected temperature of the second temperature sensor to a change in the detected temperature of the first temperature sensor,
a second temperature coefficient storage unit for storing a second temperature coefficient indicating a proportion of the change in the detected temperature of the second temperature sensor to a change in the air volume of the blower means,
an air volume change amount calculation unit for calculating an amount of change in the air volume of the blower means that is necessary to offset a change in the detected temperature of the second temperature sensor from the predetermined constant temperature, by using the first temperature coefficient stored in the first temperature coefficient storage unit and the second temperature coefficient stored in the second temperature coefficient storage unit, and
a blower means drive control unit for controlling driving of the blower means based on the amount of change in the air volume calculated by the air volume change amount calculation unit.

2. The spectrometry device according to claim 1, wherein the control unit further includes a feedback control unit for controlling driving of the blower means after drive control of the blower means based on the amount of change in the air volume calculated by the air volume change amount calculation unit, in such a way that the detected temperature of the second temperature sensor will be at the predetermined constant temperature, and wherein the blower means drive control unit further controls driving of the blower means based on an instruction from the feedback control unit.

3. The spectrometry device according to claim 1, wherein the photodetector is a photodiode array, wherein a data processing unit for processing a detection output of the photodetector is provided, and wherein the data processing unit includes a light amount change correction unit for correcting a change in an amount of light from the light source unit based on an output of a specific light receiving element of the photodiode array.

4. The spectrometry device according to claim 1, wherein, in order to cause the spectrometer to be in contact with the light source unit in a thermally conducted state, the light source chamber of the light source unit and the housing of the spectrometer are both made of thermally conductive material, and are in contact with each other through a spacer made of thermally conductive material arranged therebetween.

5. The spectrometry device according to claim 1, wherein the first temperature sensor is arranged at a position, inside the cover, that is to be directly hit by the cooling air from the blower means.

6. The spectrometry device according to claim 1, wherein the second temperature sensor is attached being in contact with an inner wall of the housing of the spectrometer.

7. The spectrometry device according to claim 1, wherein a sample cell is provided on an optical path inside the spectrometer, the sample cell allowing a measurement target sample solution from a liquid chromatograph to flow through.

8. The spectrometry device according to claim 7, wherein the photodetector is arranged at a position where light passing through the sample cell is to be detected, and the spectrometry device is an absorbance measurement device.

* * * * *